United States Patent
Wen et al.

(10) Patent No.: US 12,285,241 B2
(45) Date of Patent: Apr. 29, 2025

(54) HEART FAILURE MONITOR USING GAIT INFORMATION

(71) Applicant: Cardiac Pacemakers, Inc., St. Paul, MN (US)

(72) Inventors: Gezheng Wen, Shoreview, MN (US); Bin Mi, Arden Hills, MN (US); Qi An, Blaine, MN (US); Pramodsingh Hirasingh Thakur, Woodbury, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 950 days.

(21) Appl. No.: 16/700,462

(22) Filed: Dec. 2, 2019

(65) Prior Publication Data

US 2020/0170515 A1 Jun. 4, 2020

Related U.S. Application Data

(60) Provisional application No. 62/775,153, filed on Dec. 4, 2018.

(51) Int. Cl.
*A61B 5/0205* (2006.01)
*A61B 5/00* (2006.01)
*A61B 5/11* (2006.01)

(52) U.S. Cl.
CPC .......... *A61B 5/0205* (2013.01); *A61B 5/0077* (2013.01); *A61B 5/1112* (2013.01);
(Continued)

(58) Field of Classification Search
CPC ..... A61B 5/112; A61B 5/4023; A61B 5/0205; A61B 2562/0219; A61B 5/7271;
(Continued)

(56) References Cited

U.S. PATENT DOCUMENTS 7,844,336 B2    11/2010   Fricke et al.
8,744,587 B2 *   6/2014   Miesel ................. A61B 5/7275
                                                                    607/48
(Continued)

FOREIGN PATENT DOCUMENTS

WO    WO-2017146524 A1    8/2017

OTHER PUBLICATIONS

Byun et al. "Test-Retest Reliability and Concurrent Validity of a Single Tri-Axial Accelerometer-Based Gait Analysis in Older Adults with Normal Cognition", Jul. 2016 PLoS One (Year: 2016).*

(Continued)

*Primary Examiner* — David J. McCrosky

(74) *Attorney, Agent, or Firm* — Schwegman Lundberg & Woessner, P.A.

(57) ABSTRACT

Systems and methods for monitoring heart failure (HF) status in a patient are discussed. An exemplary system includes a gait analyzer circuit than can receive gait or balance information, and generate a gait feature such as gait speed or a gait pattern. The system includes a HF detector circuit that can detect patient HF status, or to predict patient risk of a future worsening heart failure (WHF) event, using the gait feature. In some examples, the system may trigger sensing physiologic information according to the detected gait, and detect patient HF status using the sensed physiologic information. The system can initiate or adjust a heart failure therapy according to the HF status or the WHF risk.

20 Claims, 8 Drawing Sheets

(52) U.S. Cl.
CPC ............ *A61B 5/112* (2013.01); *A61B 5/1128* (2013.01); *A61B 5/4023* (2013.01); *A61B 5/7275* (2013.01); *A61B 2562/0219* (2013.01); *A61B 2562/0223* (2013.01); *A61B 2562/0261* (2013.01)

(58) Field of Classification Search
CPC ... A61B 5/7275; A61B 5/7278; A61B 5/7282; A61B 5/7285; A61B 5/7289; A61B 5/7292; A61B 5/11; A61B 5/1104; A61B 5/1107; A61B 5/1112–1128
See application file for complete search history.

(56) References Cited

U.S. PATENT DOCUMENTS

| | | | |
|---|---|---|---|
| 9,592,379 | B2 | 3/2017 | Heruth et al. |
| 2007/0250134 | A1 | 10/2007 | Miesel et al. |
| 2010/0010361 | A1* | 1/2010 | Boute ............... A61B 5/053 600/519 |
| 2014/0303508 | A1* | 10/2014 | Plotnik-Peleg ....... A61B 5/1117 600/483 |
| 2015/0057512 | A1 | 2/2015 | Kapoor |
| 2017/0216125 | A1* | 8/2017 | Hyde .................. A61H 3/0288 |
| 2017/0293729 | A1* | 10/2017 | Movva ................ A61B 5/1121 |
| 2018/0014779 | A1 | 1/2018 | Donnelly et al. |

OTHER PUBLICATIONS

Shi, Wei Vivien, and MengChu Zhou. "Body sensors applied in pacemakers: A survey." IEEE Sensors Journal 12.6 (2011): 1817-1827. (Year: 2011).*

Goodman, Andrew D., et al., "Sustained-release oral fampridine in multiple sclerosis: a randomised, double-blind, controlled trial", The Lancet; Feb. 28, 2009: 373:732-738.

Panizzolo, Fausto Antonio, et al., "Muscle size explains low passive skeletal muscle force in heart failure patients", PeerJ, DOI 10.7717/peerj.2447, (2016), 17 pgs.

Pulignano, G., et al., "Incremental Value of Gait Speed in Predicting Prognosis of Older Adults With Heart Failure", JACC: Heart Failure, 4(4),2016, 289-298.

Schmidt, Michael D., et al., "Cardiometabolic Risk in Younger and Older Adults Across an Index of Ambulatory Activity", Am J PrevMed.2009;2009(37):4.

* cited by examiner

HEART FAILURE MONITOR USING GAIT INFORMATION

CLAIM OF PRIORITY

This application claims the benefit of priority under 35 U.S.C. § 119(e) of U.S. Provisional Patent Application Ser. No. 62/775,153, filed on Dec. 4, 2018, which is herein incorporated by reference in its entirety.

TECHNICAL FIELD

This document relates generally to medical devices, and more particularly, to systems, devices and methods for detecting worsening heart failure using patient gait information.

BACKGROUND

Congestive heart failure (CHF) is a leading cause of death in the United States and globally. CHF refers to loss of pumping power of the heart, resulting in the inability to deliver enough blood to meet the demands of peripheral tissue. CHF patients typically have enlarged heart with weakened cardiac muscles, resulting in reduced contractility and poor cardiac output of blood. CHF may be treated by drug therapy, or by an implantable medical device (IMD) such as for providing electrostimulation therapy. CHF is usually a chronic condition, but can occur suddenly. It can affect the left heart, right heart or both sides of the heart.

Some IMDs can monitor CHF patients and detect events leading to worsening heart failure (WHF). These IMDs may include or be coupled to sensors to sense physiologic signals from a patient. Frequent patient monitoring may help reduce heart failure hospitalization. Identification of patient at an elevated risk of developing WHF, such as heart failure decompensation, may help ensure timely treatment and improve prognosis and patient outcome. Identifying and safely managing the patients at elevated risk of WHF can avoid unnecessary medical interventions, hospitalization, and thereby reduce healthcare cost.

An IMD may contain electronic circuitry, such as a pulse generator, that can generate and deliver electrostimulation to excitable tissue or organs, such as a heart. The electrostimulation may help restore or improve a CHF patient's cardiac performance, or rectify cardiac arrhythmias. One example of the electrostimulation therapy is resynchronization therapy (CRT) for correcting cardiac dyssynchrony in CHF patients.

SUMMARY

This document discusses systems, devices, and methods for monitoring heart failure (HF) status using information of gait or balance of a patient during locomotion. An exemplary system includes a gait analyzer circuit to generate a gait feature, such as gait speed or a gait pattern, using gait or balance information sensed from a patient. A HF detector circuit may detect a HF status using the gait feature. The gait feature may also be used to trigger one or more physiologic sensors to sense physiologic information that can be used to detect HF status or to determine a HF risk score indicative of patient risk for experiencing a future WHF event.

Example 1 is a system for monitoring heart failure (HF) status of a patient. The system comprises a gait analyzer circuit and a HF detector circuit. The gait analyzer circuit can be configured to receive gait or balance information of a patient during locomotion, and to generate a gait feature using the received gait or balance information. The HF detector circuit can be configured to detect a HF status of the patient using the generated gait feature.

In Example 2, the subject matter of Example 1 optionally includes a motion sensor coupled to the gait analyzer circuit and configured to sense the gait or balance information of the patient, and at least one physiologic sensor configured to sense physiologic information different from the gait or balance information. The HF detector circuit can be configured to detect the HF status of the patient using the generated gait feature and the sensed physiologic information.

In Example 3, the subject matter of any one or more of Examples 1-2 optionally includes the motion sensor that can include at least one of: an accelerometer; a gyroscope; a magnetometer; an inclinometer; a goniometer; an electromagnetic tracking system; a global positioning system sensor; a force sensor; a strain gauge sensor; an electromyography sensor; or a camera configured to record an image or video of patient motion.

In Example 4, the subject matter of any one or more of Examples 2-3 optionally includes an ambulatory device that includes the motion sensor, the gait analyzer circuit, and the HF detector circuit.

In Example 5, the subject matter of any one or more of Examples 2-3 optionally includes an ambulatory device that includes the gait analyzer circuit and the HF detector circuit. The ambulatory motion sensor can be incorporated in a mobile device communicatively coupled to the implantable device.

In Example 6, the subject matter of any one or more of Examples 1-5 optionally includes the gait feature that can include one or more of: velocity; time to peak velocity; stride length; stride width; swing time; single limb support time; double limb stance; gait autonomy; cadence; foot-hip angle; or trunk-pelvis rotation angle.

In Example 7, the subject matter of any one or more of Examples 1-6 optionally includes the gait feature that can include a gait pattern indicative of a degree of continuity or an inter-limb coordination during locomotion.

In Example 8, the subject matter of any one or more of Examples 1-7 optionally includes the gait analyzer circuit that can be configured to sense body acceleration of the patient during locomotion using a multi-axis accelerometer, and to generate a multi-dimensional representation of the sensed body acceleration. The HF detector circuit can be configured to detect the HF status using the generated multi-dimensional representation.

In Example 9, the subject matter of Example 8 optionally includes the multi-dimensional representation that can include a multi-dimensional graphical representation. The HF detector circuit can be configured to detect the HF status using a geometric feature taken from the multi-dimensional graphical representation.

In Example 10, the subject matter of Example 9 optionally includes the multi-dimensional graphical representation that can include a three-dimensional (3D) contour representing body accelerations in three directions. The geometric feature can include one or more of: a location of a centroid of the 3D contour; a diameter of 3D contour; or an area or a volume of the 3D motion contour.

In Example 11, the subject matter of Example 10 optionally includes the HF detector circuit that can be configured to detect the HF status using a repeatability measure of at least a portion of the 3D contour over time.

In Example 12, the subject matter of any one or more of Examples 1-11 optionally includes the gait analyzer circuit that can be configured to identify one or more gait phases within a gait cycle, and to generate the gait feature using the received gait or balance information during the identified one or more gait phases.

In Example 13, the subject matter of any one or more of Examples 1-12 optionally includes the gait analyzer circuit that can be configured to generate a trend of the gait feature over time, and the HF detector circuit that can be configured to detect the HF status of the patient using the generated trend of the gait feature.

In Example 14, the subject matter of any one or more of Examples 1-13 optionally includes an implantable medical device (IMD) that can include one or more of the gait analyzer circuit or the HF detector circuit.

In Example 15, the subject matter of any one or more of Examples 1-14 optionally includes the HF detector circuit that can be configured to trigger one or more physiologic sensors to sense the physiologic information in response to generated gait feature satisfies a condition, and to detect the HF status further using the received physiologic information.

Example 16 is a method for monitoring heart failure (HF) status of a patient using a medical system. The method comprises steps of: receiving gait or balance information of a patient during locomotion; generating, via a gait analyzer circuit, a gait feature using the received gait or balance information; and detecting a HF status of the patient using the generated gait feature.

In Example 17, the subject matter of Example 16 optionally includes generating a trend of the gait feature over time, and receiving physiologic information different from the gait or balance information using at least one physiologic sensor. The step of detecting the HF status can include using the generated trend of the gait feature and the sensed physiologic information.

In Example 18, the subject matter of any one or more of Examples 16-17 optionally includes the gait feature that can include one or more of: velocity; time to peak velocity; stride length; stride width; swing time; single limb support time; double limb stance; gait autonomy; cadence; foot-hip angle; or a trunk-pelvis rotation angle.

In Example 19, the subject matter of any one or more of Examples 16-18 optionally includes the gait feature that can include a multi-dimensional representation of body accelerations of the patient during locomotion sensed by a multi-axis accelerometer. The step of detecting the HF status can include using the generated multi-dimensional representation.

In Example 20, the subject matter of Example 19 optionally includes the multi-dimensional graphical representation that can include a three-dimensional (3D) contour representing body accelerations in three directions. The step of detecting the HF status can include using a geometric feature taken from the 3D contour.

In Example 21, the subject matter of any one or more of Examples 16-20 optionally includes generating a statistic of multiple measurements of the gait feature. The step of detecting the HF status can include using the generated statistic of the gait feature.

In Example 22, the subject matter of any one or more of Examples 16-21 optionally includes comprising to initiating or adjusting a HF therapy in accordance with the detected HF status.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Figure 1:
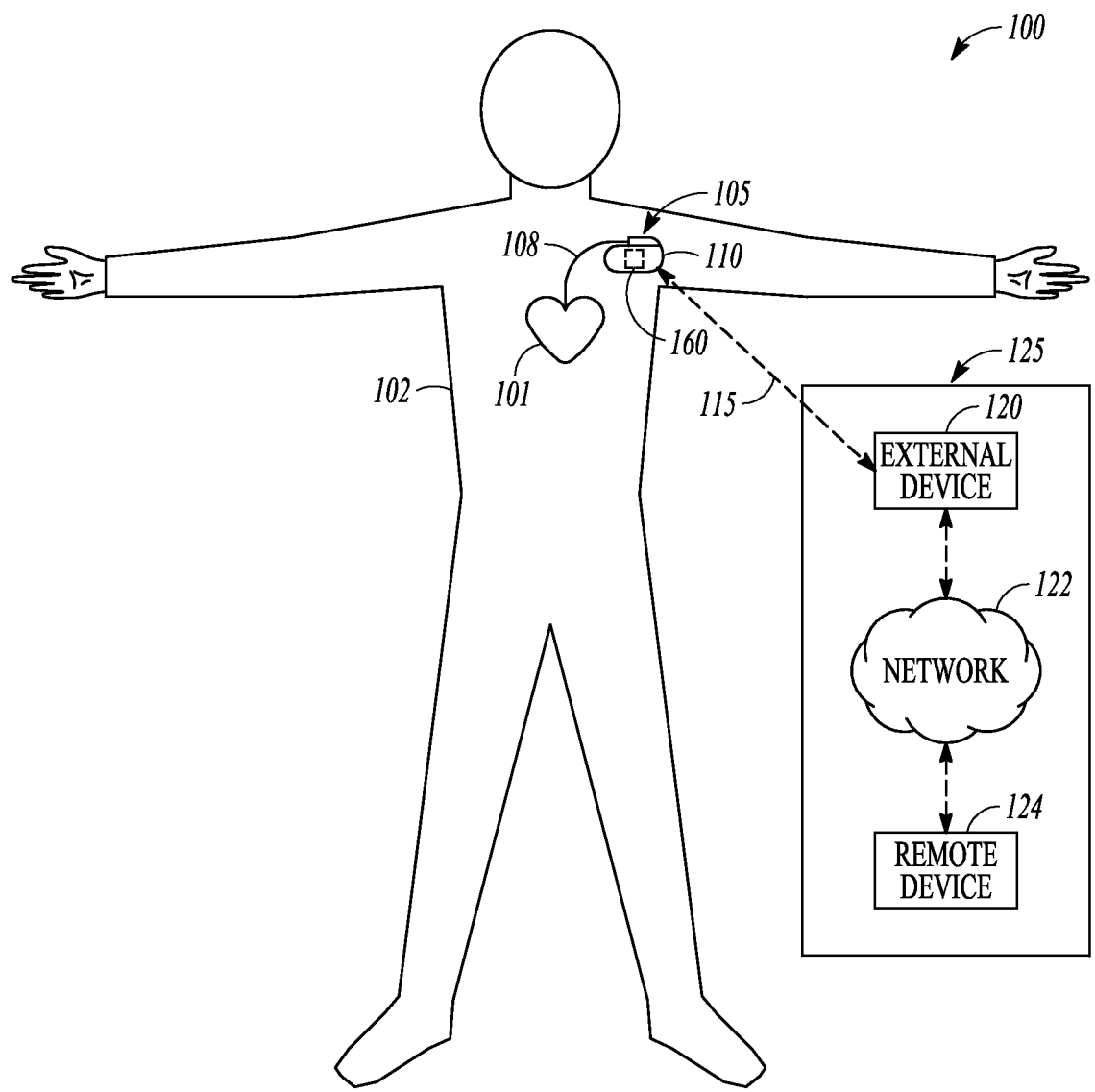
FIG. 1 illustrates generally an example of a patient monitor system and portions of an environment in which the system may operate.

Frequent monitoring of CHF patients and timely detection of intrathoracic fluid accumulation or other events indicative of heart failure decompensation status may help prevent WHF in CHF patients, hence reducing cost associated with heart failure hospitalization.

Ambulatory medical devices for monitoring heart failure patient may include implantable medical devices (IMD), subcutaneous medical devices, wearable medical devices or other external medical devices. An ambulatory medical device may be coupled to one or more physiologic sensors to sense electrical activity and mechanical function of the heart. The ambulatory medical device may optionally deliver therapy, such as electrical stimulation pulses, to the patient to restore or improve patient cardiac function. Some of these devices may provide diagnostic features, such as using transthoracic impedance or other sensor signals. For example, fluid accumulation in the lungs decreases the transthoracic impedance due to the lower resistivity of the fluid than air in the lungs. The fluid accumulation may also elevate ventricular filling pressure, resulting in a louder S3 heart sound. Additionally, fluid accumulation in the lungs may irritate the pulmonary system and leads to decrease in tidal volume and increase in respiratory rate.

Identification of patient at an elevated risk of WHF may help ensure timely intervention such as device therapy or drug therapy, thereby improving the prognosis and patient outcome. On the other hand, identifying and safely managing patients with low risk of WHF may avoid unnecessary medical interventions, thereby reducing healthcare cost. Desired performance of WHF risk stratification may include one or more of a high sensitivity, a high specificity, a high positive predictive value (PPV), or a negative predictive value (NPV). The sensitivity represents an accuracy of identifying patients with relatively a high risk of WHF. The specificity represents an accuracy of identifying patients with relatively a low risk of WHF.

Clinically, CHF may cause architectural and functional deficiencies in in skeletal muscle and reduce patient capacity of motion control. For example, CHF can reduce muscle size and strength in the lower limbs, thereby limiting one's ability to perform daily tasks and the overall poor exercise tolerance. Patients with worsened HF status may also present with poor or unbalanced posture, changes in gait pattern, restrained range of motion, or decreased intensity or duration of physical activities. Reduced walking capacity and decreased walking speed can be associated with adverse health-related events such as falls disability, hospitalization for HF, and all-cause Mortality and morbidity in older people.

A recognized challenge in HF patient management is accurate and early detection of events indicative of WHF, and identification of patients at elevated risks of WHF. The present inventors have recognized that changes in gait and disturbance in locomotion may be used to assess patient HF status, and improve the sensitivity, specificity, and predictive value of WHF event detection or WHF risk stratification. This document discusses systems, devices, and methods for monitoring patient HF status using information about gait or balance during locomotion. An exemplary system may generate a gait feature, such as gait speed or a gait pattern, using gait or balance information received from a patient, and detect a HF status using the gait feature. The system may trigger one or more physiologic sensors to sense physiologic information, and use said physiologic information, along with the gait feature, to detect patient HF status or generate a HF risk score indicative of patient risk for experiencing a future WHF event.

Various embodiments described in this document can improve the medical technology of device-based HF management, particularly computerized HF status detection and WHF risk assessment. Conventional HF detection methods face a challenge of unsatisfactory detection specificity to WHF event. The gait and balance parameters discussed herein may reduce false positive detection of WHF events, and improve the accuracy of WHF risk stratification, while at little to no additional cost or system complexity. With improved HF status assessment, hospitalization and healthcare costs associated with HF patient management may be reduced. Additionally, gait and balance information is clinically relevant to patient WHF risk. The storage of gait and balance information leads to more efficient device memory usage. With more accurate WHF risk assessment, fewer false positive WHF events may be detected, and fewer therapy interventions may be required. Accordingly, battery power can be reduced and device longevity extended, and fewer unnecessary drugs and procedures may be scheduled, prescribed, or provided. As such, overall system cost savings may be realized.

FIG. 1 illustrates generally an example of a patient monitor system 100 and portions of an environment in which the system 100 may operate. The patient monitor system 100 may chronically monitor a patient 102 to assess patient risk of developing WHF. Portions of the system 100 may be ambulatory. Portions of the system 100 may be disposed in a patient home or office, a hospital, a clinic, or a physician's office.

As illustrated in FIG. 1, the patient monitor system 100 may include an ambulatory system 105 associated with the patient 102, an external system 125, and a telemetry link 115 providing for communication between the ambulatory system 105 and the external system 125. The ambulatory system 105 may include an ambulatory medical device (AMD) 110. In an example, the AMD 110 may be an implantable device subcutaneously implanted in a chest, abdomen, or other parts of the patient 102. Examples of the implantable device may include, but are not limited to, pacemakers, pacemaker/defibrillators, cardiac resynchronization therapy (CRT) devices, cardiac remodeling control therapy (RCT) devices, neuromodulators, drug delivery devices, biological therapy devices, diagnostic devices such as cardiac monitors or loop recorders, or patient monitors, among others. The AMD 110 may include a subcutaneous medical device such as a subcutaneous monitor or diagnostic device, external monitoring or therapeutic medical devices such as automatic external defibrillators (AEDs) or Holter monitors, or wearable medical devices such as patch-based devices, smart wearables, or smart accessories.

By way of example and not limitation, the AMD 110 may be coupled to a lead system 108. The lead system 108 may include one or more transvenously, subcutaneously, or non-invasively placed leads or catheters. Each lead or catheter may include one or more electrodes. The arrangements and uses of the lead system 108 and the associated electrodes may be determined using the patient need and the capability of the AMD 110. The associated electrodes on the lead system 108 may be positioned at the patient's thorax or abdomen to sense a physiologic signal indicative of cardiac activity, or physiologic responses to diagnostic or therapeutic stimulations to a target tissue. By way of example and not limitation, and as illustrated in FIG. 1, the lead system 108 may be surgically inserted into, or positioned on the surface of, a heart 101. The electrodes on the lead system 108 may be positioned on a portion of a heart 101, such as a right atrium (RA), a right ventricle (RV), a left atrium (LA), or a left ventricle (LV), or any tissue between or near the heart portions. In some examples, the lead system 108 and the associated electrodes may alternatively be positioned on other parts of the body to sense a physiologic signal containing information about patient heart rate or pulse rate. In an example, the ambulatory system 105 may include one or more leadless sensors not being tethered to the AMD 110 via the lead system 108. The leadless ambulatory sensors may be configured to sense a physiologic signal and wirelessly communicate with the AMD 110.

The AMD 110 may include a hermetically sealed can that houses one or more of a sensing circuit, a control circuit, a communication circuit, and a battery, among other components. The sensing circuit may sense a physiologic signal, such as using a physiologic sensor or the electrodes associated with the lead system 108. The physiologic signals may contain information about patient physiologic response to a precipitating event associated with onset of a future WHF event. The physiologic signal may represent changes in patient hemodynamic status. Examples of the physiologic signal may include one or more of electrocardiogram, intracardiac electrogram, arrhythmia, heart rate, heart rate variability, intrathoracic impedance, intracardiac impedance, arterial pressure, pulmonary artery pressure, left atrial pressure, right ventricular (RV) pressure, left ventricular (LV) coronary pressure, coronary blood temperature, blood oxygen saturation, one or more heart sounds, intracardiac acceleration, physical activity or exertion level, physiologic response to activity, posture, respiratory rate, tidal volume, respiratory sounds, body weight, or body temperature.

The AMD 110 may include a risk assessment circuit 160 configured to assess a patient risk of developing a worsened chronic disease or condition, such as a WHF event. The risk assessment circuit 160 may receive gait or balance information of a patient during locomotion, among other physiologic information of the patient, such as via one or more physiologic sensors. In an example, the risk assessment circuit 160 may trend the gait or balance measurements over time, generate a gait feature, and detect patient HF status or generate a HF risk score using the gait feature, optionally further using other physiologic information of the patient. The HF risk indicator indicates patient risk of developing a future WHF event, such as a heart failure decompensation event. In various examples, the risk assessment circuit 160 may also be configured to detect worsening of other diseases or conditions including, for example, cardiac arrhythmias, syncope, respiratory disease such as COPD or asthma, or renal dysfunctions, among other medical conditions.

The AMD 110 may include a therapy unit that may generate and deliver a therapy to the patient. The therapy may be preventive (e.g., to prevent development into a full-blown condition, decompensation, etc.), or therapeutic (e.g., to treat heart failure or alleviate complications) in nature, and may modify, restore, or improve patient physiologic functionalities. Examples of the therapy may include electrical, magnetic, or other forms of therapy. In some examples, the AMD 110 may include a drug delivery system such as a drug infusion pump device to deliver drug therapy to the patient. In some examples, the AMD 110 may monitor patient physiologic responses to the delivered to assess the efficacy of the therapy.

The external system 125 may include a dedicated hardware/software system such as a programmer, a remote server-based patient management system, or alternatively a system defined predominantly by software running on a standard personal computer. The external system 125 may manage the patient 102 through the AMD 110 connected to the external system 125 via a communication link 115. This may include, for example, programming the AMD 110 to perform one or more of acquiring physiologic data, performing at least one self-diagnostic test (such as for a device operational status), analyzing the physiologic data to generate a WHF risk indicator, or optionally delivering or adjusting a therapy to the patient 102. The external system 125 may communicate with the AMD 110 via the communication link 115. The device data received by the external system 125 may include real-time or stored physiologic data from the patient 102, diagnostic data, responses to therapies delivered to the patient 102, or device operational status of the AMD 110 (e.g., battery status and lead impedance). The communication link 115 may be an inductive telemetry link, a capacitive telemetry link, or a radio-frequency (RF) telemetry link, or wireless telemetry based on, for example, "strong" Bluetooth or IEEE 802.11 wireless fidelity "WiFi" interfacing standards. Other configurations and combinations of patient data source interfacing are possible.

By way of example and not limitation, the external system 125 may include an external device 120 in proximity of the AMD 110, and a remote device 124 in a location relatively distant from the AMD 110 in communication with the external device 120 via a telecommunication network 122. Examples of the external device 120 may include a programmer device. The network 122 may provide wired or wireless interconnectivity. In an example, the network 122 may be based on the Transmission Control Protocol/Internet Protocol (TCP/IP) network communication specification, although other types or combinations of networking implementations are possible. Similarly, other network topologies and arrangements are possible.

The remote device 124 may include a centralized server acting as a central hub for collected patient data storage and analysis. The patient data may include data collected by the AMD 110, and other data acquisition sensors or devices associated with the patient 102. The server may be configured as a uni-, multi- or distributed computing and processing system. In an example, the remote device 124 may include a data processor configured to perform heart failure detection or risk stratification using patient gait or balance information received by the AMD 110. Computationally intensive algorithms, such as machine-learning algorithms, may be implemented in the remote device 124 to process the data retrospectively to detect WHF or analyze patient WHF risk. The remote device 124 may generate an alert notification. The alert notifications may include a Web page update, phone or pager call, E-mail, SMS, text or "Instant" message, as well as a message to the patient and a simultaneous direct notification to emergency services and to the clinician. Other alert notifications are possible.

One or more of the external device 120 or the remote device 124 may output the WHF detection or the WHF risk to a system user such as the patient or a clinician. The external device 120 or the remote device 124 may include respective display for displaying the physiologic data acquired by the AMD 110. The physiologic data may be presented in a table, a chart, a diagram, or any other types of textual, tabular, or graphical presentation formats. The external device 120 or the remote device 124 may include a printer for printing hard copies of signals and information related to the generation of WHF risk indicator. The presentation of the output information may include audio or other media formats. In an example, the output unit 254 may generate alerts, alarms, emergency calls, or other forms of warnings to signal the system user about the WHF detection or WHF risk. The clinician may review, perform further analysis, or adjudicate the WHF detection or WHF risk. The WHF detection or the WHF risk, optionally along with the data acquired by the AMD 110 and other data acquisition sensors or devices, may be output to a process such as an instance of a computer program executable in a microprocessor. In an example, the process may include an automated generation of recommendations for initiating or adjusting a therapy, or a recommendation for further diagnostic test or treatment.

Portions of the AMD 110 or the external system 125 may be implemented using hardware, software, firmware, or combinations thereof. Portions of the AMD 110 or the external system 125 may be implemented using an application-specific circuit that may be constructed or configured to perform one or more functions, or may be implemented using a general-purpose circuit that may be programmed or otherwise configured to perform one or more functions. Such a general-purpose circuit may include a microprocessor or a portion thereof, a microcontroller or a portion thereof, or a programmable logic circuit, a memory circuit, a network interface, and various components for interconnecting these components. For example, a "comparator" may include, among other things, an electronic circuit comparator that may be constructed to perform the specific function of a comparison between two signals or the comparator may be implemented as a portion of a general-purpose circuit that may be driven by a code instructing a portion of the general-purpose circuit to perform a comparison between the two signals.

Figure 2:
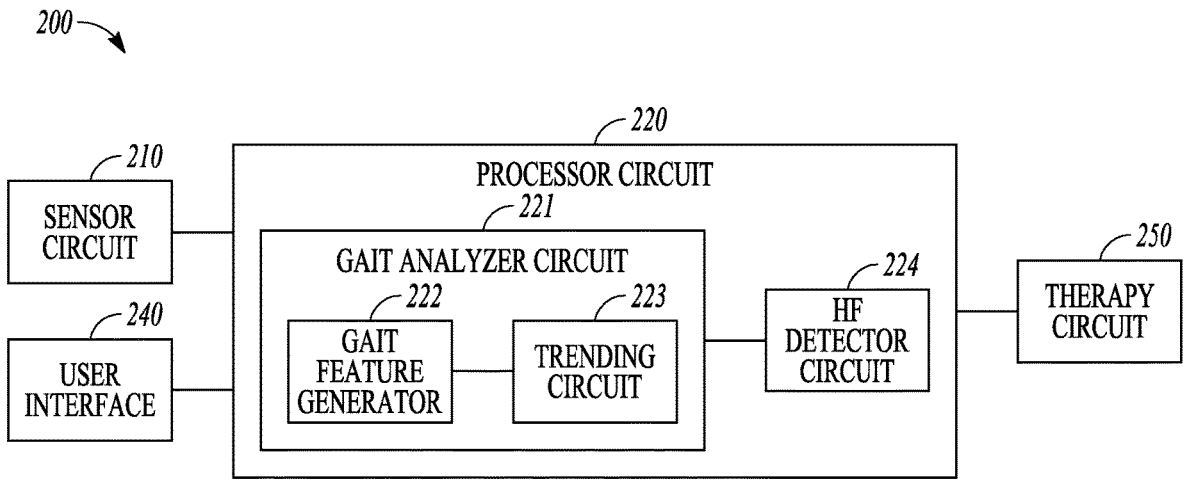
FIG. 2 illustrates generally an example of a heart failure (HF) monitor system to assess patient HF status.

FIG. 2 illustrates generally an example of a heart failure monitor system 200 to assess patient HF status. At least a portion of the heart failure monitor system 200 may be implemented in the AMD 110, the external system 125 such as one or more of the external device 120 or the remote device 124, or distributed between the AMD 110 and the external system 125. The heart failure monitor system 200 may include one or more of a sensor circuit 210, a processor circuit 220, a user interface 240, and an optional therapy circuit 250 for delivering a HF therapy.

The sensor circuit 210 may be coupled to an implantable, wearable, or otherwise ambulatory sensor or electrodes associated with the patient. The sensor may be incorporated into, or otherwise associated with an ambulatory device such as the AMD 110. The sensor circuit 210 may include a sense amplifier circuit to sense at least one physiologic or functional signal from a patient. Examples of the physiologic or functional signals may include surface electrocardiography (ECG) sensed from electrodes placed on the body surface, subcutaneous ECG sensed from electrodes placed under the skin, intracardiac electrogram (EGM) sensed from the one or more electrodes on the lead system 108, heart rate signal, physical activity signal, or posture signal, a thoracic or cardiac impedance signal, arterial pressure signal, pulmonary artery pressure signal, left atrial pressure signal, RV pressure signal, LV coronary pressure signal, coronary blood temperature signal, blood oxygen saturation signal, heart sound signal, physiologic response to activity, apnea hypopnea index, one or more respiratory signals such as a respiratory rate signal or a tidal volume signal, brain natriuretic peptide (BNP), blood panel, sodium and potassium levels, glucose level and other biomarkers and bio-chemical markers, among others. In some examples, the physiologic or functional signals sensed from a patient may be stored in a storage device, such as an electronic medical record system, and the sensor circuit 210 may be configured to receive a stored physiologic signal from the storage device in response to a user input or triggered by a specific event. The sensor circuit 210 may pre-process the sensed physiologic or functional signals, including, for example, amplification, digitization, filtering, or other signal conditioning operations.

In various examples, the sensor circuit 210 may be coupled to a motion sensor to sense one or more motor activity signals during locomotion. Examples of the motor activity signals may include gait or balance, posture, physical activity, among other motor activities. The motion sensor may be an accelerometer, a gyroscope, a magnetometer, an inclinometer, a goniometer, an electromagnetic tracking system (ETS), a global positioning system (GPS) sensor, a force sensor, a strain gauge sensor, or an electromyography (EMG) sensor, among others. The motion sensor may be an ambulatory sensor, such as an implantable or wearable sensor associated with the patient, or a holdable sensor such as one implemented in a mobile device carried by the patient. In some examples, the motion sensor may be a stationary sensor that can be mounted in a room or attached to furniture, and configured to detect a motor activity signal from the patient when the patient enters or moves about an environment of the patient's daily life. Examples of the sensors for detecting various motor activity signals are discussed below, such as with reference to FIG. 3.

The processor circuit 220 may generate a WHF risk indicator using the sensed motor activity signal, such as the gait or balance signal. The processor circuit 220 may be implemented as a part of a microprocessor circuit, which may be a dedicated processor such as a digital signal processor, application specific integrated circuit (ASIC), microprocessor, or other type of processor for processing information including physical activity information. Alternatively, the microprocessor circuit may be a general-purpose processor that may receive and execute a set of instructions of performing the functions, methods, or techniques described herein.

The processor circuit 220 may include circuit sets comprising one or more other circuits or sub-circuits, including a gait analyzer circuit 221 and a HF detector circuit 224. These circuits or sub-circuits may, alone or in combination, perform the functions, methods or techniques described herein. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

The gait analyzer circuit 221 may include a gait or balance feature generator 222 configured to generate one or more signal metrics using the sensed motor activity signal. The generated signal metrics are indicative of patient motor control or kinetics, such as gait, balance, posture, physical activity, range of motion, among others. The signal metrics may include statistical parameters extracted from the sensed motor activity signal, such as signal mean, median, mode, or other central tendency measures or a histogram of the signal intensity, among others. The signal metrics may additionally or alternatively include morphological parameters such as maximum or minimum, or variability within a specific time period such as a cardiac cycle, positive or negative slope or higher order statistics, or signal power spectral density at a specific frequency range, among other morphological parameters. In some examples, the gait analyzer circuit 221 may additionally include timing information such as a time interval between a first characteristic point in one signal and a second characteristic point in another signal.

The gait or balance feature generator 222 may generate the signal metrics using a time-domain method, such as zero-crossing counting or peak detection from the sensed motor activity signal to generate a gait feature, such as a step rate or a gait speed. The signal metrics may be generated in a frequency domain or other transformation domain, such as using Fast Fourier Transform or discrete wavelet transform. For example, frequency content of the gait or balance may be extracted and used to determine gait speed or step rate, or to recognize different gait patterns. Additionally or alternatively, the signal metrics may be generated using machine learning methods, such as K-means clustering, Hidden Markov models, among other methods, to detect and characterize cyclic dynamics of locomotion. Examples of gait feature detection are discussed below with reference to FIGS. 5A-5D.

In some examples, the gait analyzer circuit 221 may be configured to identify one or more gait phases within a gait cycle. A gait cycle is a repetitive pattern including steps and strides. A step is one single step, a stride is a whole gait cycle. The step time is the time between heel strike of one leg and heel strike of the contralateral leg. The gait analyzer circuit 221 may recognize a stance phase (which occupies about 60% of the gait cycle) and a swing phase (which occupies about 40% of the gait cycle) of a gait cycle. Alternatively, more detailed classification may be used, such as the phases of Heel Strike, Foot Flat, Mid-Stance, Heel-Off, Toe-Off, and Mid-Swing. The gait or balance feature generator 222 may generate respective gait features during one or more of the identified gait phases.

The gait feature, optionally along with other motor activity features, may be used to adaptively control sensing and processing of the gait or balance signal. In an example, the sensed gait or balance signal may be filtered through a filter circuit. One or more cutoff frequencies of the filter circuit may be adjusted automatically in accordance with a gait speed, a gait pattern, or other gait features. For example, a wider passband, or a higher low-pass cutoff frequency, can be used at elevated gait speed. In some examples, the gait feature may be used to adaptively control the gait or balance analysis. For example, a threshold for detecting steps or identifying a particular gait phase may be adjusted in accordance with a gait speed, a gait pattern, or other gait features.

The gait analyzer circuit 221 may include an optional trending circuit 223 to generate a trend of the gait feature over time. Examples of the gait feature trend include a walking speed trend, stride length trend, stride width trend, swing time trend, cadence trend, among others. In some examples, the gait analyzer circuit 221 may trend multiple gait features respectively, and generate a composite gait trend using a linear or nonlinear combination of the multiple gait or balance trends. The composite trend may be more predictive of progression of HF status than an individual feature trend. The gait analyzer circuit 221 may classify patient gait into one of gait categories using the gait feature or the trend of the gait feature, such as healthy gait, slow and steady gait, imbalanced gait, motor impairment, among other categories.

The heart failure detector circuit 224, coupled to the gait analyzer circuit 221, may be configured to detect patient HF status using the generated gait feature, or the trend of the gain or balance feature. In some examples, the heart failure detector circuit 224 may generate a WHF risk indicator indicating a risk level of developing a future WHF event. Reduced walking capacity and poor exercise tolerance may be associated with deteriorated HF status. Patients with worsening HF status may more likely present with poor or unbalanced posture, abnormal gait pattern, intermittent or variable gaits (such as due to reduced ability of gait control), restrained range of motion, or decreased intensity or duration of physical activities. Therefore, characterization of changes in patient gait, optionally along with other motor activity signals, as discussed herein may enhance the accuracy and reliability of early detection of WHF event, or WHF risk stratification.

The heart failure detector circuit 224 may detect patient HF status using a comparison between the gait feature and a detection criterion, such as a threshold or a value range. The heart failure detector circuit 224 may classify patient WHF risk into one of a plurality of risk categories. In an example, the heart failure detector circuit 224 may generate a WHF risk indicator (R) (e.g., a risk score) using a pre-determined mapping f of a plurality of gait features ($X_1$, $X_2$, ..., $X_K$), that is, $R=f(X_1, X_2, ..., X_K)$, where K denotes the number of the gait features. In an example, the mapping f may be represented by a look-up table or an association map, where each pre-determined WHF risks, R(i), is associated with the K gait features falling within respective value ranges, denoted by $X_1(i), X_2(i), ..., X_K(i)$. Additionally or alternatively, the heart failure detector circuit 224 may determine the WHF risk indicator using a weighted combination of the gait features, trends of two or more gait features, and optionally other motor activity features or other physiologic signal metrics. The weight factors may be determined using performance of gait features in predicting the patient WHF risk. The weight factors may also be determined using population data.

In some examples, the gait analyzer circuit 221 may generate a statistic using multiple measurements of a gait feature, or from the gait feature trend. Examples of the statistic may include total counts, maximum, minimum, or percentage of certain speed or stride length during a day or a specified time period during a day, mean, median, or other central tendency measurements, variance or other second or higher-order statistics, histogram or statistical distribution, among others. The HF detector circuit 224 may detect patient HF status or to determine patient WHF risk using the generated statistic of the gait feature.

The gait feature may be used to trigger one or more physiologic sensors to sense physiologic information, such as when the gait feature satisfies a specific condition. In an example, the sensor circuit 210 may sense one or more cardiac, pulmonary, neural, or biochemical signals when a gait feature falls within a specified value range. The processor circuit 220 may generate one or more physiological signal metrics from the sensed physiologic signal, and the heart failure detector circuit 224 may detect HF status, or generate a WHF risk indicator, using a combination of the gait feature and the physiological signal metrics. Examples of the triggered physiologic signals may include an electrocardiograph (ECG), intracardiac electrogram, gyrocardiography, magnetocardiography, a heart rate signal, a heart rate variability signal, a cardiovascular pressure signal, a heart sounds signal, a respiratory signal, a thoracic impedance signal, or a respiratory sounds signal, among others.

The user interface 220 may include a display unit and a user input device. In an example, at least a portion of the user interface 240 may be implemented in the external system 125. The input device may include a keyboard, an on-screen keyboard, a mouse, a trackball, a touchpad, a touch-screen, or other pointing or navigating devices. A user, such as the patient or a clinician, may use the input device to enter information about patient information such as patient demographics, medical history, or other medical information. A user may program one or more parameters for system components, such as the sensing circuit 210, the gait analyzer circuit 221, the heart failure detector circuit 224, or the therapy circuit 240. The display unit may be configured to display sensed gait or balance signal or other motor activity signals or physiologic signals, trends of the signal metric, or any intermediary results. The information may be presented in a table, a chart, a diagram, or any other types of textual, tabular, or graphical presentation formats, for displaying to a system user. The presentation of the output information may include audio or other media format. In an example, the output unit 242 may generate alerts, alarms, emergency calls, or other forms of warnings to signal the system user about the pain score.

The optional therapy circuit 250 may deliver a therapy to the patient in response to the detection of a WHF event, or the WHF risk satisfying a condition such as exceeding the risk threshold. In an example, the system 200 may include a detector circuit configured to detect a WHF event, such as a heart failure decompensation event, using the WHF risk indicator. The detector may select one or more physiologic signals or signal metrics based on the WHF risk indicator, and use the selected signals or signal metrics to detect a WHF event. In another example, the detector may generate a composite index using a combination of physiologic signals or signal metrics each weighted by respective weight factors. The weight factors may be determined based on the WHF risk indicator. The therapy circuit 250 may deliver a therapy in response to the detection of WHF event. Examples of the therapy may include electrostimulation therapy delivered to the heart, a nerve tissue, among other target tissue, a cardioversion therapy, a defibrillation therapy, or drug therapy. In some examples, the therapy circuit 250 may modify an existing therapy, such as adjust a stimulation parameter or drug dosage.

Although the discussion herein focuses on WHF risk, this is meant only by way of example but not limitation. Systems, devices, and methods discussed in this document may also be suitable for detecting various sorts of diseases or for assessing risk of developing other worsened conditions, such as cardiac arrhythmias, heart failure decompensation, pulmonary edema, pulmonary condition exacerbation, asthma and pneumonia, myocardial infarction, dilated cardiomyopathy, ischemic cardiomyopathy, valvular disease, renal disease, chronic obstructive pulmonary disease, peripheral vascular disease, cerebrovascular disease, hepatic disease, diabetes, anemia, or depression, among others.

Figure 3:
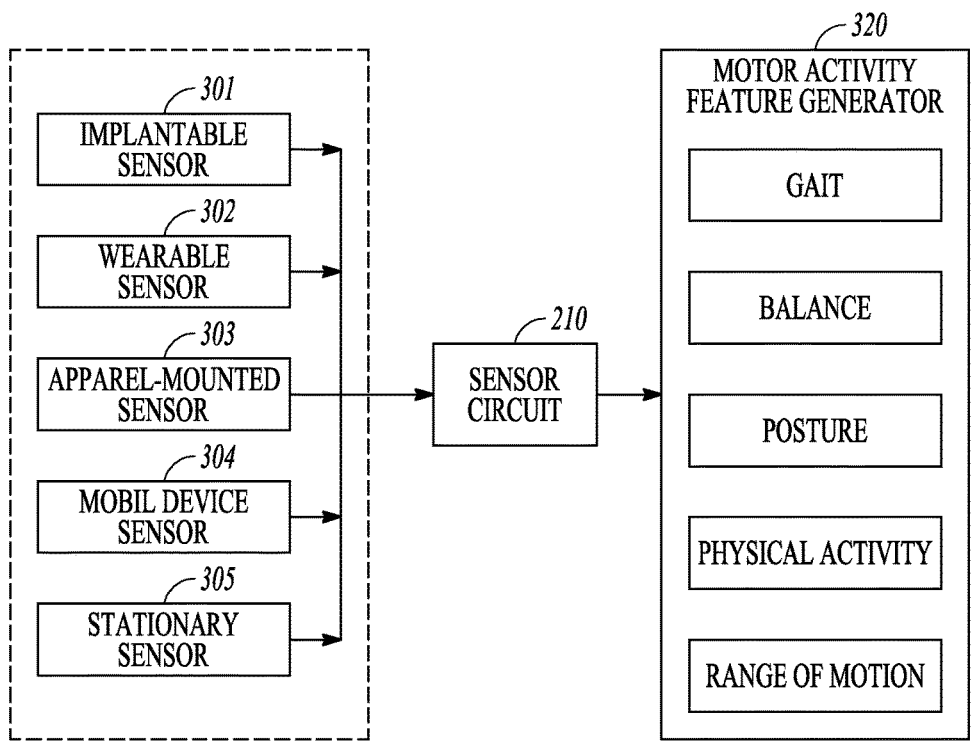
FIG. 3 illustrates generally an example of a portion of a HF detection system for sensing gait or balance of a patient, among other motor activity signals.

FIG. 3 illustrates generally an example of a portion of a HF detection system for sensing gait or balance of a patient, among other motor activity signals. The system portion may generate signal metrics including motor activity metrics, which may be used by the system 200 to detect a WHF event or to assess patient WHF risk. The system portion may include one or more motion sensors 301 through 305, the sensor circuit 210, and a motor activity feature generator 320, which can be an embodiment of the gait analyzer circuit 221.

The motion sensors may include one or more of an implantable sensor 301, a wearable sensor 302, an apparel-mounted sensor 303, a mobile device sensor 304, or a stationary sensor 305. The implantable sensor 301 may be subcutaneously implanted at various body locations. The wearable sensor 302 may be worn on the head, wrist, hand, foot, ankle, waist, or other parts of the body. The apparel-mounted sensor 303 may be mounted on a garment, a footwear, a headwear, or one or more accessories carried by the patient, such as a pendant, a necklace, or a bracelet. In an example, the apparel-mounted sensor 303 may include insole force sensor for placement inside a shoe or a boot. The insole force sensor may take the form of a strain gauge, piezoelectric sensor, or capacitive sensor, among others. The insole force sensor may be wirelessly coupled to the sensor circuit 210 or the IMD 110. The sensor circuit 210 may be configured to analyze force distribution on a patient's foot and generate an indicator of gait.

The mobile device sensor 304 can be a sensor incorporated in a mobile device. Examples of the mobile device may include a smart phone, a wearable device, a fitness band, a portable health monitor, a tablet, a laptop computer, or other types of portable computerized device. In an example, embedded in a mobile device may include motion sensors such as an accelerometer, a gyroscope, a magnometer, a GPS sensor or other location services, or a camera that sense motor activity signals. The mobile device may be communicatively coupled to the processor circuit 220 or the IMB 110 via a communication link such as a universal serial bus (USB) connection, a Bluetooth protocol, Ethernet, IEEE 802.11 wireless, an inductive telemetry link, or a radio-frequency telemetry link, among others.

The stationary sensor 305 may be positioned in an environment of patient's daily life such as at a bedside, in a room at patient home, or in a testing room at a clinic or medical facility. In an example, the motion sensors may be mounted on a chair, a bed (e.g., under or attached to a mattress), or a fixture in a patient's environment. Unlike the implantable, wearable, or apparel-mounted sensors which are ambulatory in nature, the stationary sensor 305 are configured to detect one or more motor activity signals when the patient enters, or remains within, an environment within the scope of surveillance of the stationary sensor 305. Examples of the stationary sensor 305 may include a camera or a video recorder configured to capture an image, an image sequence, or a video of the patient at a specific physical state, such as sitting, standing, walking, or doing physical activities. In an example, the camera may be an infrared camera. In an example, the camera is a digital camera that may generate digital data representation of an image or a video sequence. The motor activity feature generator 320 may generate from the image data image features associated with patient posture, gait, balance, range of motion, etc.

The sensor circuit 210 may be coupled to the one or more motion sensors 301-305 via a wired or wireless connection. The sensor circuit 210 may pre-process the sensed motor activity signal. From the processed motor activity signals, the motor activity feature generator 320 may extract one or more motor activity features, such as gait, balance, posture, physical activity, or range of motion, among others. In an example, the sensor circuit 210 may be coupled to a posture sensor to detect signals of a posture, a state of balance, or a range of motion of the patient. Examples of the posture sensor may include a tilt switch or a single- or multi-axis accelerometer configured to be affiliated with the patient in one of the sensor types 301-305. For example, the posture sensor may be disposed external to the body or implanted inside the body. Posture may be represented by, for example, a tilt angle. In some examples, posture or physical activity information may be derived from thoracic impedance information. The motor activity feature generator 320 may generate from the posture signal one or more signal metrics including body position during sitting, standing, or walking. Additionally or alternatively, the sensor circuit 210 may be coupled to a motion sensor positioned on the extremities or the trunk of patient body to detect range of motion. The motor activity feature generator 320 may generate signal metrics of lumbar forward flexion, shoulder flexion, elbow flexion, rotation of arm and elbow joint, trunk-pelvis rotation, foot-hip angle, or other motor control and kinematic metrics. The range of motion metrics may also include indicators of smoothness of motion, such as a rate or a pattern of change in motion with respect to time, or with respect to angular velocity, etc. A decrease in activity intensity or duration from an activity baseline such as established using patient historical activity signals, or less frequent transition or an increase in transition time from one activity to another may be earlier indications of worsening HF.

In another example, the sensor circuit 210 may be coupled to an accelerometer to sense a physical activity signal. The accelerometer may be a single-axis or a multi-axis accelerometer, and configured to be associated with the patient in a manner corresponding to one of the sensor types of 301-305. Examples of the accelerometer may include flexible piezoelectric crystal (e.g., quartz) accelerometer or capacitive accelerometer, fabricated using micro electromechanical systems (MEMS) technology. The motor activity feature generator 320 may generate from the physical activity signal one or more signal metrics including activity intensity, activity duration, or a transition time between different types of activities. A decrease in activity intensity or duration from an activity baseline such as established using patient historical activity signals, or less frequent transition or an increase in transition time from one activity to another may indicate worsening HF of a patient.

The sensor circuit 210 may be coupled to a gait sensor to detect gait of the patient. The sensors may be worn or attached to various parts of the patient's body, such as on the foot, ankle, leg, waist, or other parts on the torso or the extremities. Examples of the gait sensors may include accelerometer, gyroscope (which may be a one-, two-, or three-axis gyroscope), magnetometer (e.g., a compass), inclinometers, goniometers, electromagnetic tracking system (ETS), a global positioning system (GPS) sensor or other location services, sensing fabric, force sensor, strain gauges, and sensors for electromyography (EMG). The motor activity feature generator 320 may generate gait features using signals acquired from a single sensor type or a combined sensor system of multiple types of sensors. Examples of gait features may include velocity, time to peak velocity, step length, stride length, stride width, swing time, single limb support time, double limb stance, gait autonomy, cadence, trunk-pelvis rotation, foot-hip angle, among other measurements.

In some examples, the gait feature may include a gait pattern. Examples of the gait pattern may include an antalgic gait including decreased step length, and significantly shortened stance phase relative to the swing phase to avoid weight bearing on the involved side; an ataxic gait characterized by staggering and unsteady and uncoordinated walk with a broad standing base; a choreiform gait characterized by irregular, jerky, and involuntary movements occur in all extremities; a diplegic gait characterized by bilateral involvement and spasticity in all extremities; a double-step gait in which alternate steps of a different length or a at a different rate; an equine pattern characterized by high steps usually during excessive activity of the gastrocnemius; a festinating gait involving walking on toes as though pushed; a spastic gait with stiff movements and legs being held together, and slightly flexed hip and knees; among others. In an example, the gait pattern may be characterized by a measure of continuity during locomotion, such as the presence and/or degree of intermittence or interruptions during locomotion. In an example, the gait pattern may be characterized by a measure of inter-limb coordination during locomotion. In some examples, the gait pattern may be characterized by a multi-dimensional representation of motion (e.g., acceleration) in different directions. The multi-dimensional representation can be a graphical representation, such as a two- or three-dimensional plot. The gait pattern can be represented by geometric measurements or morphological features extracted from the multidimensional graphical representation, examples of which are discussed below with reference to FIGS. 6A-6B.

Figure 4:
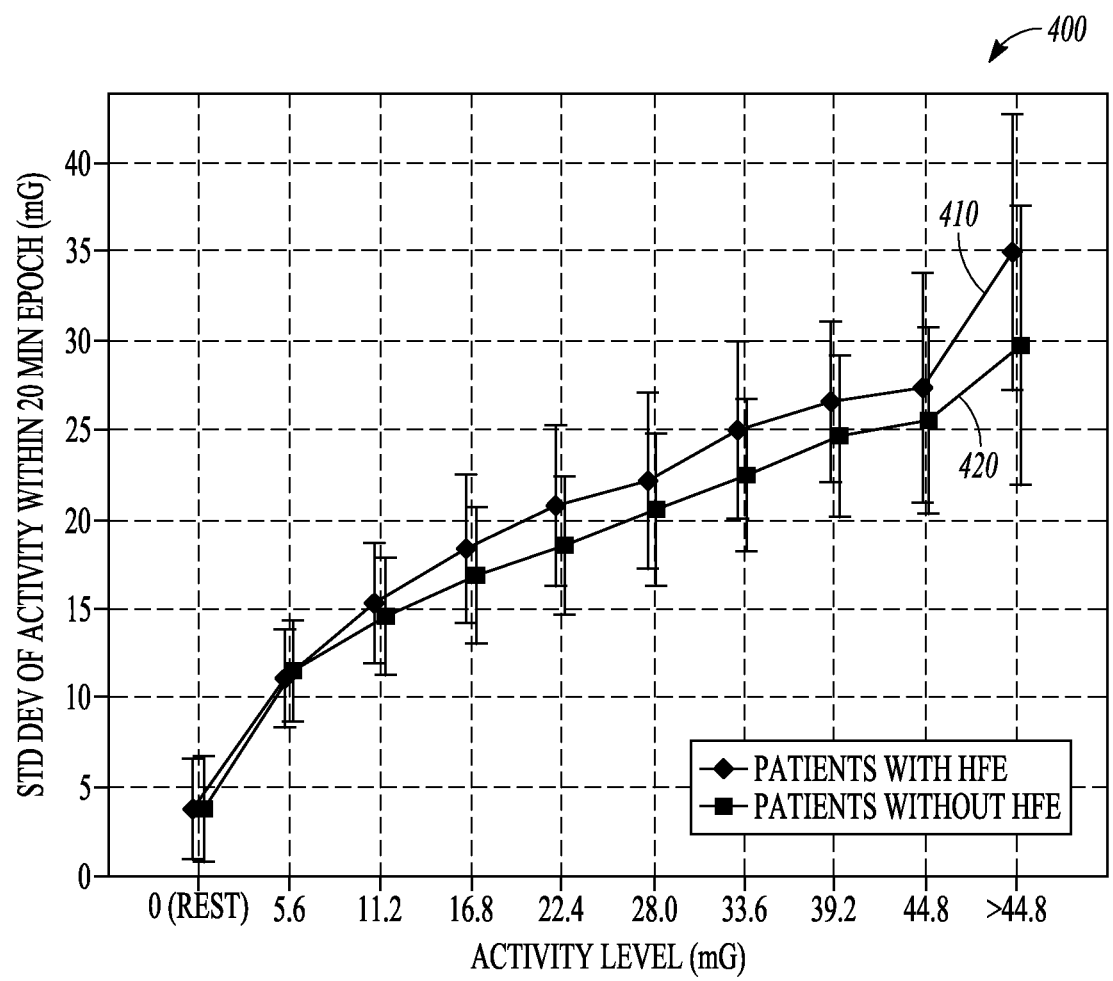
FIG. 4 is a graph illustrating variability of gait during physical activity in patients who have experienced heart failure events (HFE) and in HFE-free subjects.

FIG. 4 is a graph 400 illustrating variability of physical activity intensity in a group of patients who have experienced heart failure events (HFE) (curve 410) and in another group of HFE-free subjects (curve 420). The variability of physical activity intensity represents a level of consistency of physical exertion, such as continuity of locomotion, a gait pattern that can be used for detecting patient HF status or for predicting patient WHF risk. As illustrated in FIG. 4, the physical activity variability can be measured using an accelerometer when the HF patients and HFE-free subjects undergo physical activities at different physical activity levels. The physical activity level (shown in the horizontal axis) can be expressed in terms of acceleration in milli-Gravity (mG). The physical activity variability (shown in the vertical axis) can be measured using a standard deviation of multiple acceleration measurements within a specified time period (e.g., a 20-minute epoch) at a given range of activity level. The graph 400 shows that the HF patients (curve 410) undergoing this test generally have a higher variability in physical activity intensity than the HFE-free subjects. Moreover, the distinction between the two groups of test takers is more prominent at higher activity levels. This suggests that compared to the HFE-free subjects, the HF patients generally have a higher inconsistency level of physical exertion, and low continuity of locomotion (e.g., more frequent interruptions and intermittent walking/gaits), particularly during more strenuous physical activities. The detector circuit 224 may detect patient HF status or to predict a WHF risk if the physical activity variability or a trend of the physical activity variability at one or more activity levels exceeds a respective threshold.

Figure 5A:
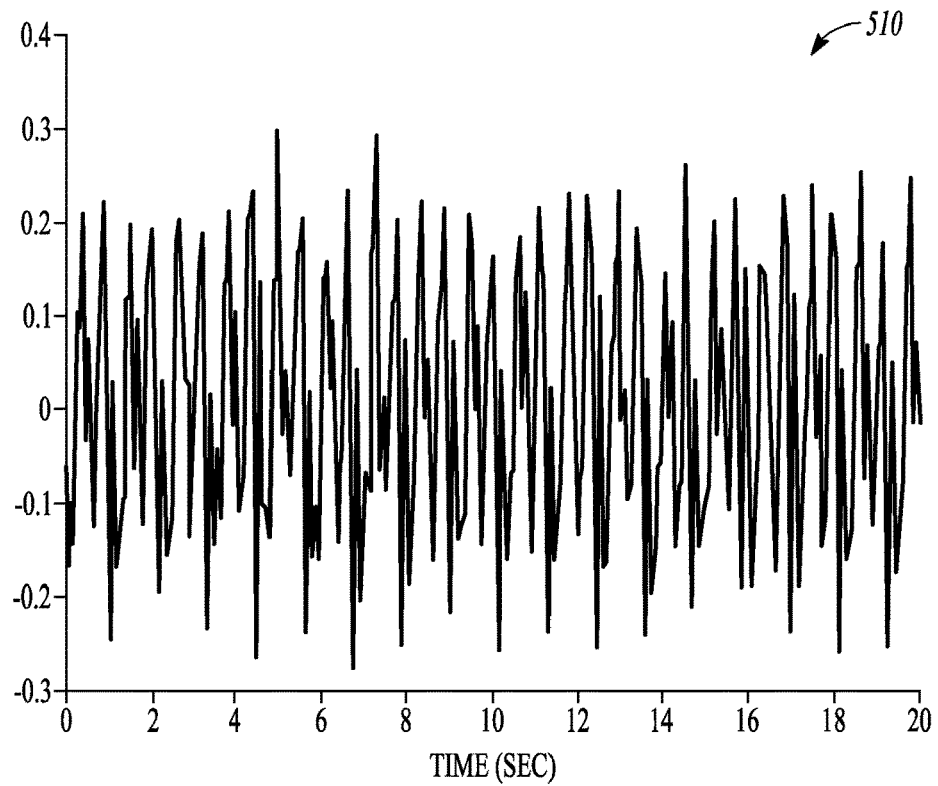
FIGS. 5A-5D illustrate exemplary accelerometer signals representing motions of a HF patient with HFE and a HFE-free subject during normal walking and gait features extracted from the autocorrelation sequences.
Figure 5B:
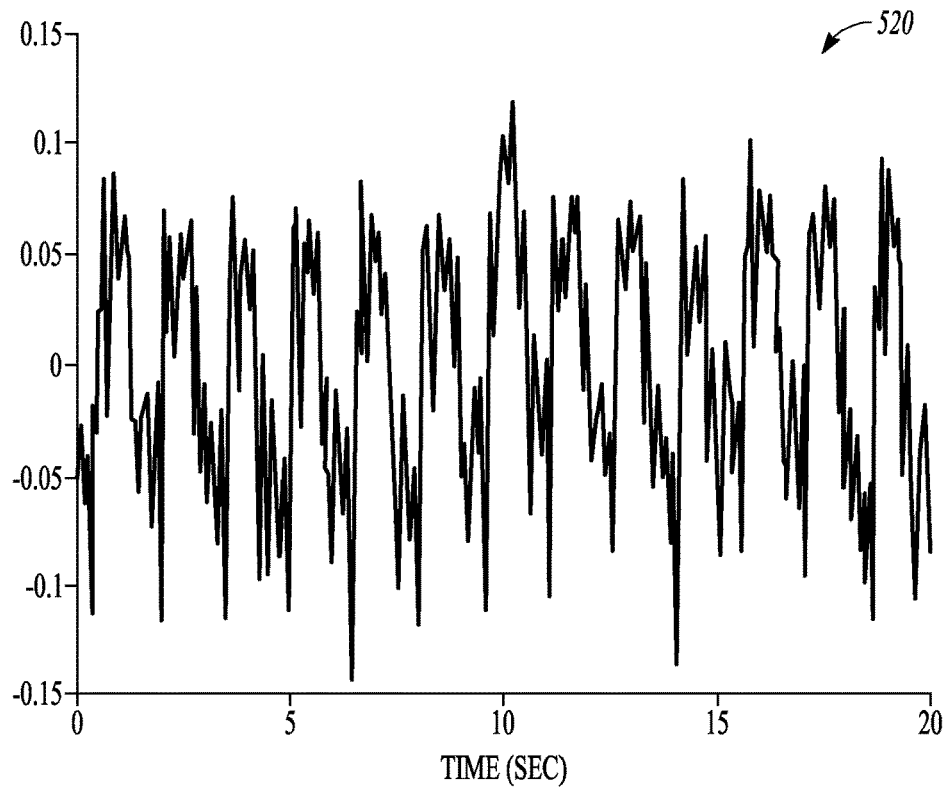
Figure 5C:
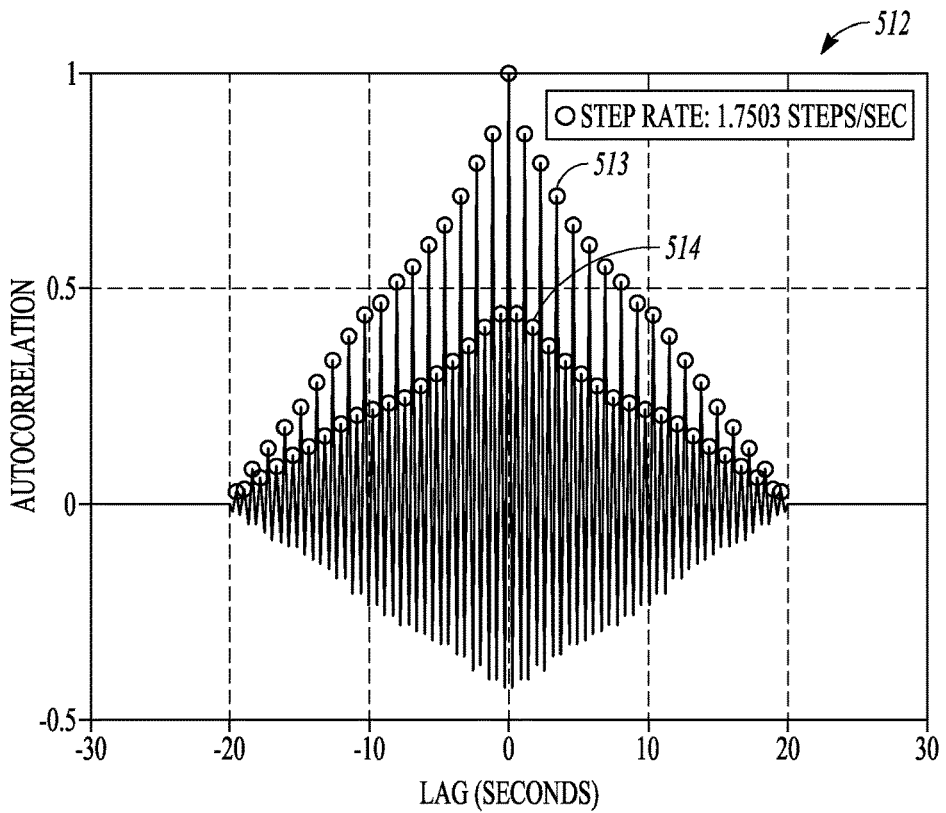
Figure 5D:
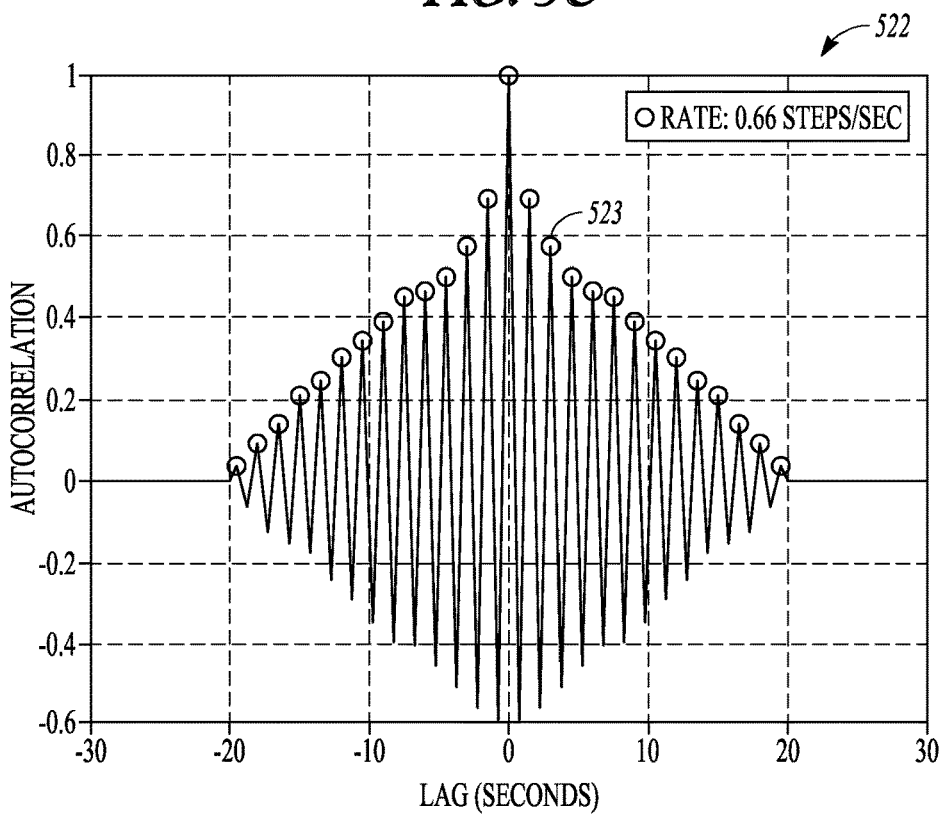

FIGS. 5A-5D illustrate exemplary accelerometer signals representing motions of a HF patient with HFE and a HFE-free subject during normal walking and gait features extracted from the autocorrelation sequences. In particular, the acceleration signal 510 as shown in FIG. 5A represents motion of a healthy subject free of HFE, and the acceleration signal 520 as shown in FIG. 5B represents motion of a HF patient with HFE. Autocorrelation analyses can be carried out respectively on the acceleration signals 510 and 520, such as using the gait analyzer circuit 221. FIG. 5C illustrates an autocorrelation sequence 512, and FIG. 5D illustrates an autocorrelation sequence 522 of the acceleration signal 520, at different time lags. One or more gait features may be extracted from the time-domain signals 510 and 520, or alternatively from the autocorrelation sequences 512 and 522. In an example, periodicity of the repeating locomotion patterns can be detected using the autocorrelation sequences, such as based on the autocorrelation peaks. The time lag corresponding to the autocorrelation peaks represents duration of a gait cycle. Other features, such as velocity or step rate (i.e., steps per second) or pace, may be determined using the gait cycle.

The autocorrelation sequence 512 shows two alternating patterns of motion. A first pattern, represented by the autocorrelation peaks 513, repeats periodically at a longer time interval ($\Delta 1$). The time interval $\Delta 1$ corresponds to stride time, the time interval of a full gait cycle (e.g., between a left foot strike and next left foot strike (L-L interval), or between a right foot strike and next right foot strike (R-R interval)). A second pattern, represented by the autocorrelation peaks 514, repeats periodically at a shorter interval ($\Delta 2$). The interval $\Delta 2$ corresponds to step time, the time interval between heel strike of one foot and the immediate subsequent heel strike of the contralateral foot (e.g., L-R interval, or R-L interval). As illustrated in FIG. 5C, the autocorrelation peaks 514 are interlaced within the autocorrelation peaks 513. The step time Δ2 is approximately one-half of the stride time Δ1, indicating that the L-R interval is approximately equal to the R-L interval, both counting for one-half of a gait cycle. The presence of the two distinct motions patterns suggests that the FIFE-free subject has a high degree of temporal coordination between left and right legs during locomotion. The autocorrelation peaks 514 also have smaller amplitudes than the autocorrelation peaks 513. Because autocorrelation peak amplitude is indicative of similarity of acceleration signals at different time lag, the smaller amplitudes of the autocorrelation peaks 514 suggests that the FIFE-free healthy subject has distinct motion strength between left and right heel strikes during locomotion.

In contrast, the autocorrelation sequence 522 obtained from accelerometer signal taken from the HF patient experiencing HFE does not have the distinct motion patterns as manifested in the autocorrelation sequence 521. Instead, only one motion pattern can be identified from the autocorrelation sequence 522, which repeats periodically at an interval (Δ3), as represented by the autocorrelation peaks 523, The interval Δ3 represents a gait cycle. The step time Δ3 of the HF patient is longer than the stride time Δ1 and the step time Δ2 and of the HFE-free subject, suggesting that the HF patient has a slower step speed. The HF patient also has a shorter stride length, and is more likely dragging or pacing during locomotion. Moreover, the absence of different patterns of autocorrelation peak amplitudes (such as peaks 513 and 514 in FIG. 5C) suggests that the HF patient lacks distinct motion strengths between left and right heel strikes during locomotion.

The gait analyzer circuit 221 may generate one or more gait features from the autocorrelation sequences 512 and 522, such as gait cycle length, presence or absence of the distinct motion patterns (e.g., distinct autocorrelation peak amplitude patterns), velocity, or step rate (i.e., expressed as steps per second). For example, walking velocity can be determined to be approximately 1.75 steps per second for HFE-free subject according to the autocorrelation sequence 512, and approximately 0.66 steps per second for the HF patient experiencing HFE according to the autocorrelation sequence 522. The HF detector circuit 224 may detect patient HF status or to predict a WHF risk using one or more these features.

Figure 6A:
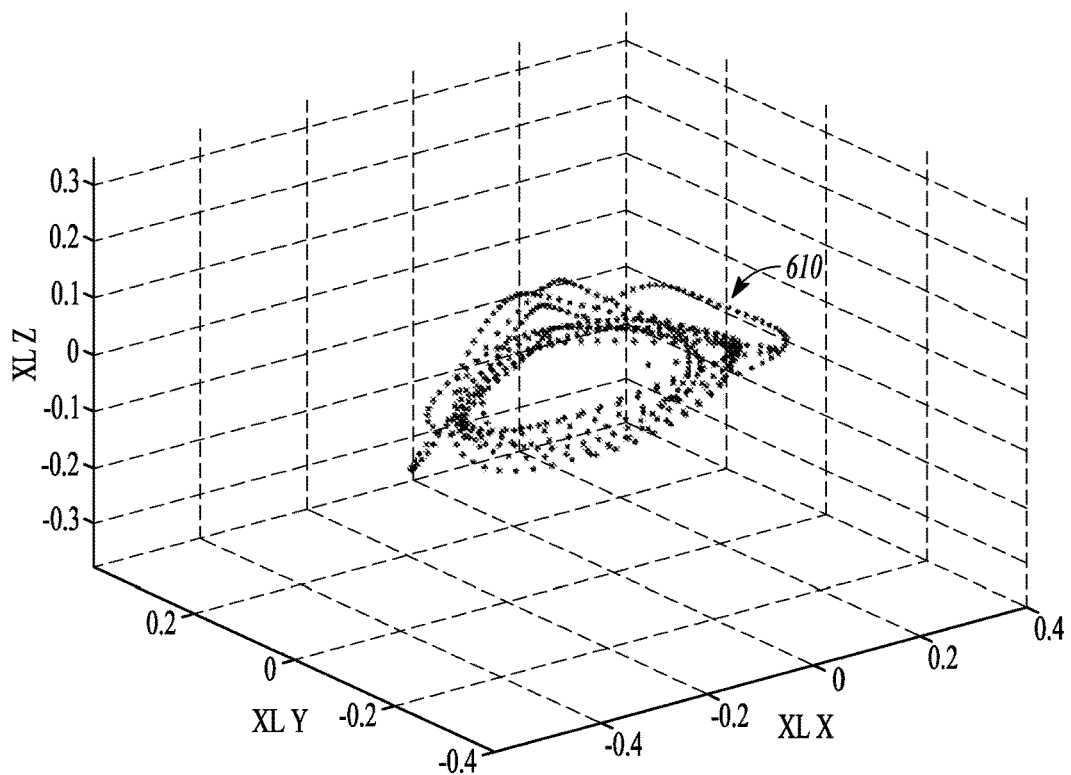
FIGS. 6A-6B are graphs illustrating gait patterns represented by acceleration signals in three dimensions collected from HF patients with HFE and in HFE-free subjects during normal walking.
Figure 6B:
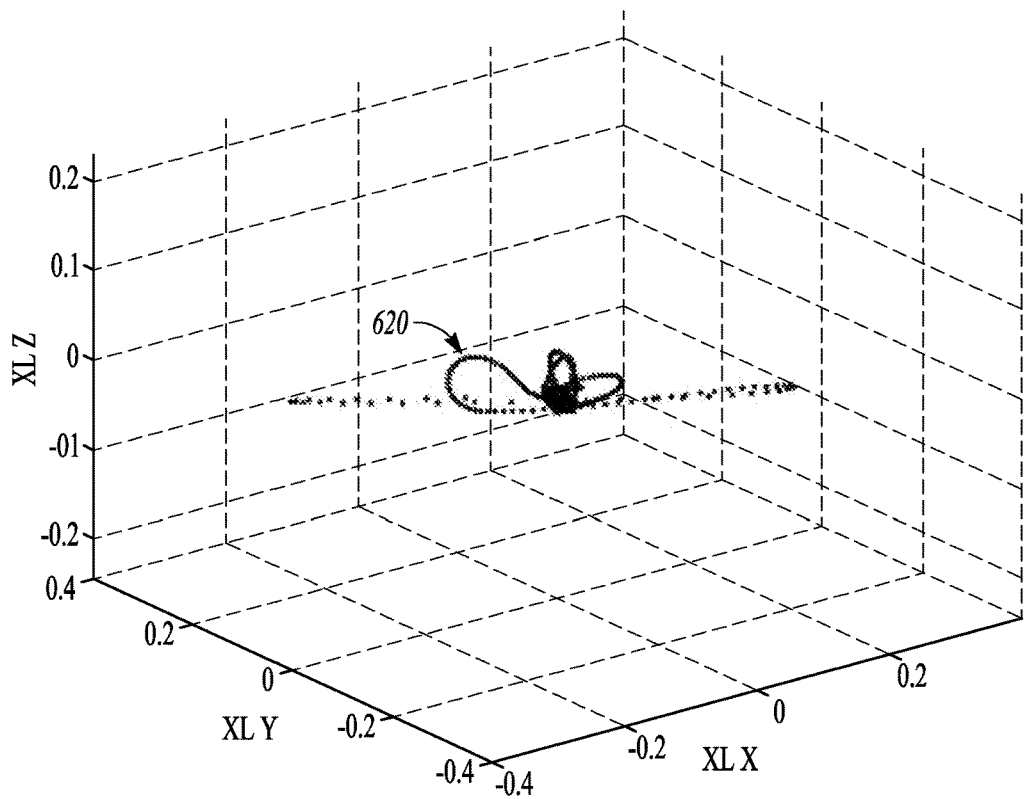

FIGS. 6A-6B are graphs illustrating gait patterns represented by acceleration (XL) signals in three dimensions (X, Y, and Z) collected from HF patients with HFE and in HFE-free subjects during normal walking. The XL signals were recorded using ambulatory three-axis accelerometers, which are configured to sense and acquire acceleration data in three directions: lateral-medial ($XL_X$), cranial-caudal ($XL_Y$), and ventral-dorsal directions ($XL_Z$). The acceleration data is collected for a specified time period (e.g., 5 seconds), and a three-dimensional (3D) acceleration plot representing $XL_X$, $XL_Y$, and $XL_Z$ at different time can be generated. The 3D acceleration plot 610 as illustrated in FIG. 6A is generated using acceleration data collected from a HFE-free subject, and the 3D acceleration plot 620 as illustrated in FIG. 6B is generated using acceleration data collected from a HF patient with HFE.

One or more gait feature may be generated from the 3D acceleration plots 610 and 620, each representing a 3D motion contour. As illustrated in FIG. 6A, the 3D motion contour of the HFE-free subjects has a circle-like shape and repeats itself over time with a high degree of regularity. In contrast, the 3D motion contour of the HF patients as shown in FIG. 6B lacks a regular shape or a distinct repetitive pattern, and varies substantially over time. The gait or balance feature generator 222 may generate geometric or morphological features from the 3D acceleration plots 610 and 620. Examples of such features may include a location of a centroid of the 3D motion contour, a diameter of 3D motion contour, an area or a volume of the 3D motion contour, among others. The HF detector circuit 224 may detect patient HF status or to predict a WHF risk using a comparison of the geometric or morphological features to a threshold or other detection criteria. Additionally or alternatively, the gait or balance feature generator 222 may generate a morphology variability or other repeatability measure of at least a portion of the 3D motion contour over time. The HF detector circuit 224 may detect a WHF event or predict an elevated WHF risk if the morphological variability exceeds a threshold, indicating low regularity and inter-limb coordination during locomotion as seen in patients with worsened HF status.

Figure 7:
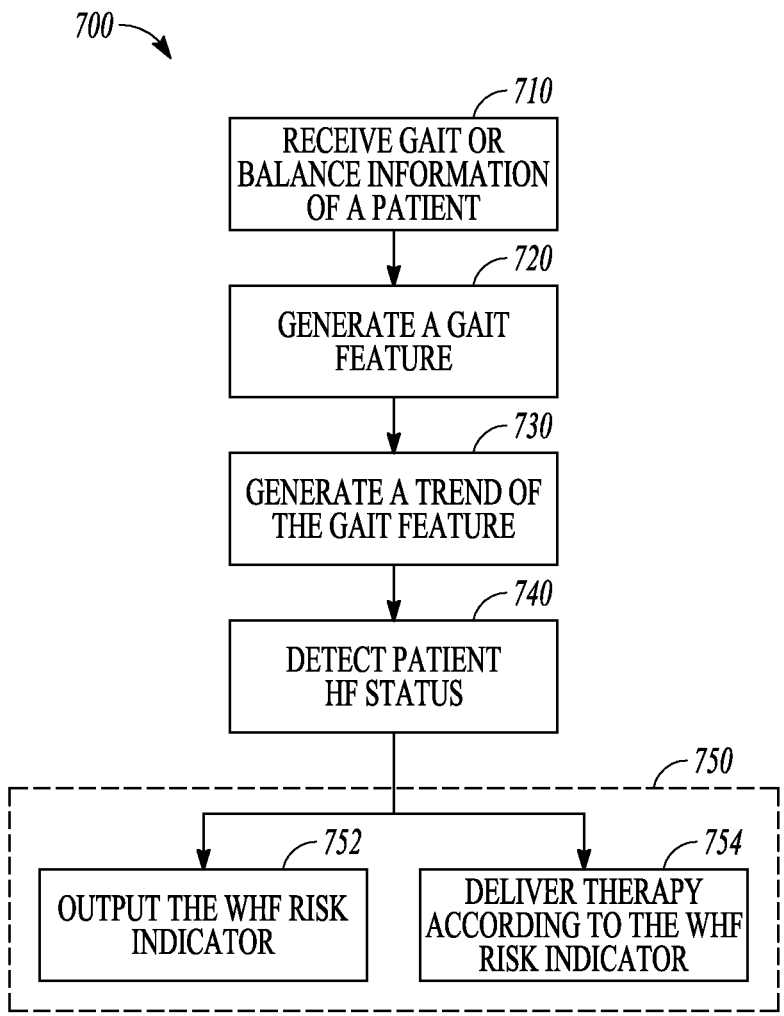
FIG. 7 is a flowchart illustrating an example of a method for assessing HF status using gait information of a patient.

FIG. 7 illustrates generally an example of a method 700 for assessing heart failure (HF) status using gait or balance information of a patient. The method 700 may be implemented and executed in an ambulatory medical device (AMD), such as an implantable or wearable medical device, or in a remote patient management system. In various examples, the method 700 may be implemented in and executed by the AMD 110, one or more devices in the external system 125, or the heart failure monitor system 200 or a modification thereof.

The method 700 commences at step 710, where gait or balance information of a patient may be received. In an example, the gait or balance information includes motions signals during locomotion sensed using a motion sensor, such as an accelerometer, a gyroscope, a magnetometer, an inclinometer, a goniometer, an electromagnetic tracking system (ETS), a global positioning system (GPS) sensor, a force sensor, a strain gauge sensor, or an electromyography (EMG) sensor. The motion sensor may be an implantable sensor, a wearable sensor, an apparel-mounted sensor, a sensor incorporated into a mobile device, or a stationary sensor, such as described above with reference to FIG. 3. In some examples, the motor activity signals acquired from a patient may be stored in a storage device, such as an electronic medical record system, and can be retrieved from the storage device in response to a user command or triggered by a specific event.

At 720, a gait feature may be generated using the received gait or balance information, such as using the gait or balance feature generator 222. Statistical, morphological, or timing metrics may be extracted from the sensed motor activity signals. These signal metrics may be generated using time-domain methods, frequency-domain methods, or machine-learning methods, as discussed above with reference to FIG. 2. From the signal metrics, one or more gait features may be generated, along with other signal metrics indicative of patient motor control or kinetics, such as physical activity features, balance features, posture features, and range of motion features, as described above with reference to FIG. 3. Examples of gait features may include velocity, time to peak velocity, step length, stride length, stride width, swing time, single limb support time, double limb stance, gait autonomy, cadence, trunk-pelvis rotation, foot-hip angle, among other measurements. The gait features may include a gait pattern, such as an antalgic pattern, an ataxic gait, a choreiform gait, a diplegic gait, a double-step gait, a festinating gait, or a spastic gait, among others. The gait pattern may be characterized by a measure of continuity, or a measure of inter-limb coordination, during locomotion. In some examples, the gait pattern may include a multi-dimensional representation of accelerations during locomotion sensed by an ambulatory multi-axis accelerometer. In an example, the multi-dimensional graphical representation includes a three-dimensional (3D) contour representing accelerations in three directions, such as illustrated in FIG. 6. In some examples, one or more gait phases within a gait cycle may be identified, such as a stand phase and a swing phase. Respective gait features during one or more of the identified gait phases may be generated.

At 730, one or more gait features may be trended over time. Examples of the gait feature trend may include a walking speed trend, stride length trend, stride width trend, swing time trend, cadence trend, among others. A composite gait trend may be generated using a linear or nonlinear combination of the multiple gait or balance trends. In some examples, according to the gait feature or the trend of the gait feature, a patient gait may be classified into one of gait categories, such as healthy gait, slow and steady gait, imbalanced gait, motor impairment, among other categories.

At 740, patient HF status, such as a worsening HF status, may be detected using the gait feature or the trend of the gait feature. In some examples, a WHF risk indicator may be generated, which is indicative of patient risk of experiencing a future WHF event. In an example, the detection of HF status may include comparing the gait feature to a detection criterion, such as a threshold value or a value range. The heart failure detector circuit 224 may classify patient WHF risk into a risk category. In an example, a WHF risk indicator may be generated using a pre-determined mapping of a plurality of gait features to corresponding WHF risk indicators (e.g., risk scores). In another example, the WHF risk indicator may be generated using a weighted combination of the gait features, trends of two or more gait features, and optionally other physiologic signal metrics. In some examples, the detection of the HF status or a projection of patient WHF risk may include using a statistic of multiple measurements of a gait feature or from the gait feature trend.

In some examples, the detection of HF status (e.g., detection of a WHF event) may include using a WHF risk indicator. One or more physiologic signals may be selected based on the WHF risk indicator. In an example, a composite detection index may be generated using the WHF risk-indicated signals or signal metrics. A WHF event is detected if the composite detection index satisfies a specific detection condition, such as exceeding a detection threshold. In an example, the composite detection index may be determined using a combination of physiologic signals or signal metrics each weighted by respective weight factors. The weight factors may be determined based on the WHF risk indicator.

At 750, the detected HF status or the WHF risk indicator may be output to a user or a process. At 752, a human-perceptible presentation may be generated, and displayed on a display screen of the user interface 240. The information may be presented in a table, a chart, a diagram, or any other types of textual, tabular, or graphical presentation formats. Hard copies of signals and information related to the detected HF status may be printed. In an example, alerts, alarms, emergency calls, or other forms of warnings may be generated to warn the system user about the detected HF status, or an elevated WHF risk. The WHF detection or the WHF risk may be output to a process such as an instance of a computer program executable in a microprocessor. Additionally or alternatively, at 754, the detected HF status or the WHF risk may trigger a therapy delivered to the patient, such as using the therapy circuit 250. The therapy may be delivered to the patient in response to the WHF risk satisfying a condition, such as exceeding the risk threshold. Examples of the therapy may include electrostimulation therapy delivered to the heart, nerve, or other target tissue, a cardioversion therapy, a defibrillation therapy, or drug therapy. In some examples, an existing therapy may be modified, such as by adjusting a stimulation parameter or drug dosage.

Figure 8:
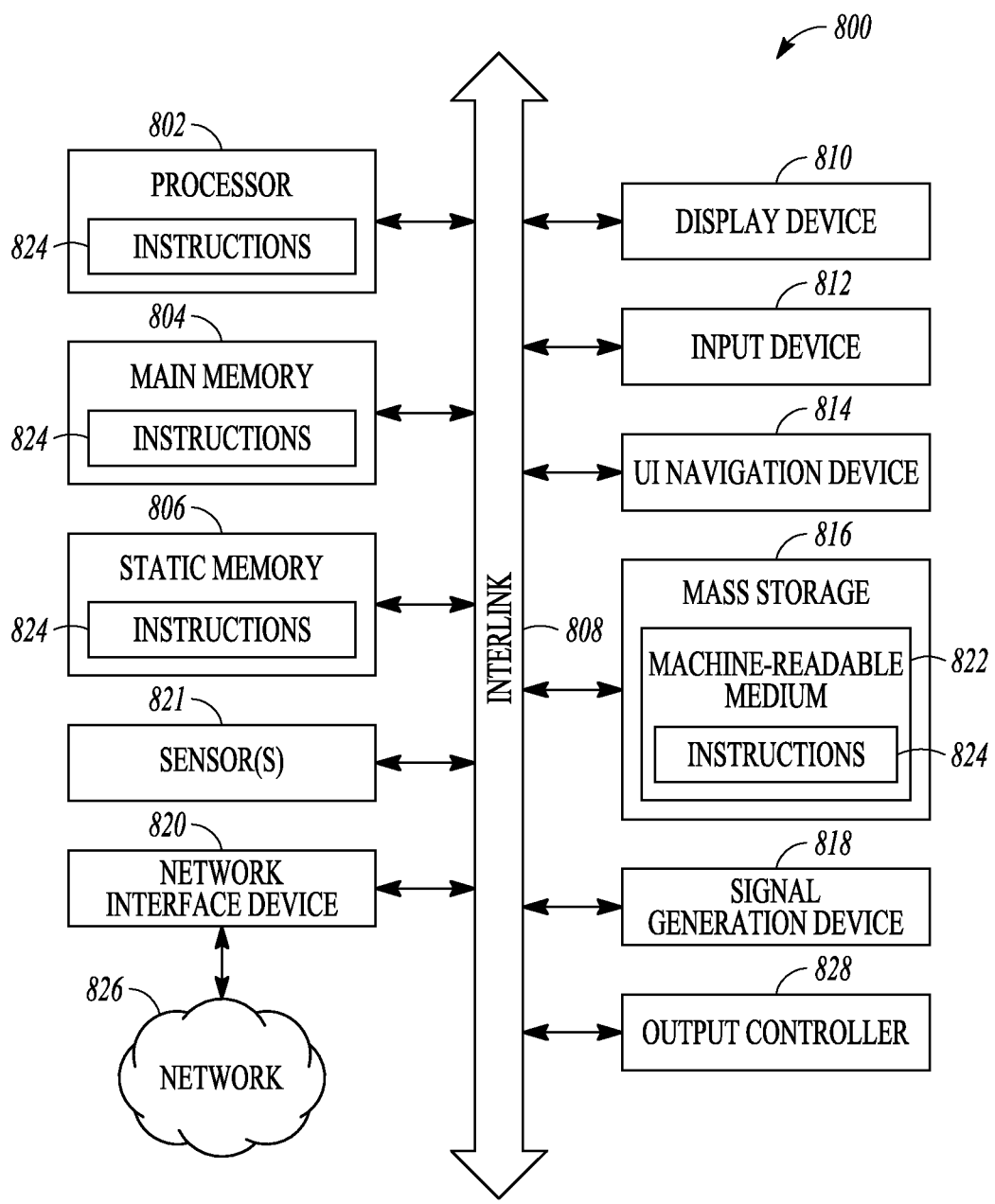
FIG. 8 illustrates generally a block diagram of an example machine upon which any one or more of the techniques discussed herein may perform.

FIG. 8 illustrates generally a block diagram of an example machine 800 upon which any one or more of the techniques (e.g., methodologies) discussed herein may perform. Portions of this description may apply to the computing framework of various portions of the LCP device, the IMD, or the external programmer.

In alternative embodiments, the machine 800 may operate as a standalone device or may be connected (e.g., networked) to other machines. In a networked deployment, the machine 800 may operate in the capacity of a server machine, a client machine, or both in server-client network environments. In an example, the machine 800 may act as a peer machine in peer-to-peer (P2P) (or other distributed) network environment. The machine 800 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specific operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 800 may include a hardware processor 802 (e.g., a central processing unit (CPU), a graphics processing unit (GPU), a hardware processor core, or any combination thereof), a main memory 804 and a static memory 806, some or all of which may communicate with each other via an interlink (e.g., bus) 808. The machine 800 may further include a display unit 810 (e.g., a raster display, vector display, holographic display, etc.), an alphanumeric input device 812 (e.g., a keyboard), and a user interface (UI) navigation device 814 (e.g., a mouse). In an example, the display unit 810, input device 812 and UI navigation device 814 may be a touch screen display. The machine 800 may additionally include a storage device (e.g., drive unit) 816, a signal generation device 818 (e.g., a speaker), a network interface device 820, and one or more sensors 821, such as a global positioning system (GPS) sensor, compass, accelerometer, or other sensors. The machine 800 may include an output controller 828, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 816 may include a machine readable medium 822 on which is stored one or more sets of data structures or instructions 824 (e.g., software) embodying or utilized by any one or more of the techniques or functions described herein. The instructions 824 may also reside, completely or at least partially, within the main memory 804, within static memory 806, or within the hardware processor 802 during execution thereof by the machine 800. In an example, one or any combination of the hardware processor 802, the main memory 804, the static memory 806, or the storage device 816 may constitute machine-readable media.

While the machine-readable medium 822 is illustrated as a single medium, the term "machine readable medium" may include a single medium or multiple media (e.g., a centralized or distributed database, and/or associated caches and servers) configured to store the one or more instructions 824.

The term "machine readable medium" may include any medium that is capable of storing, encoding, or carrying instructions for execution by the machine 800 and that cause the machine 800 to perform any one or more of the techniques of the present disclosure, or that is capable of storing, encoding or carrying data structures used by or associated with such instructions. Non-limiting machine-readable medium examples may include solid-state memories, and optical and magnetic media. In an example, a massed machine-readable medium comprises a machine readable medium with a plurality of particles having invariant (e.g., rest) mass. Accordingly, massed machine-readable media are not transitory propagating signals. Specific examples of massed machine-readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 824 may further be transmitted or received over a communications network 826 using a transmission medium via the network interface device 820 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as WiFi®, IEEE 802.16 family of standards known as WiMax®), IEEE 802.15.4 family of standards, peer-to-peer (P2P) networks, among others. In an example, the network interface device 820 may include one or more physical jacks (e.g., Ethernet, coaxial, or phone jacks) or one or more antennas to connect to the communications network 826. In an example, the network interface device 820 may include a plurality of antennas to communicate wirelessly using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 800, and includes digital or analog communications signals or other intangible medium to facilitate communication of such software.

Various embodiments are illustrated in the figures above. One or more features from one or more of these embodiments may be combined to form other embodiments.

The method examples described herein can be machine or computer-implemented at least in part. Some examples may include a computer-readable medium or machine-readable medium encoded with instructions operable to configure an electronic device or system to perform methods as described in the above examples. An implementation of such methods may include code, such as microcode, assembly language code, a higher-level language code, or the like. Such code may include computer readable instructions for performing various methods. The code can form portions of computer program products. Further, the code can be tangibly stored on one or more volatile or non-volatile computer-readable media during execution or at other times.

The above detailed description is intended to be illustrative, and not restrictive. The scope of the disclosure should, therefore, be determined with references to the appended claims, along with the full scope of equivalents to which such claims are entitled.

What is claimed is:

1. A system for monitoring heart failure (HF) status of a patient, the system comprising:
   a gait analyzer circuit configured to receive gait or balance information of a patient during locomotion, to generate a first gait feature and a second gait feature different than the first gait feature using the received gait or balance information, and to generate a first trend of the first gait feature over time and a second trend of the second gait feature over time; and
   a HF detector circuit configured to determine respective weight factors for the first and second gait features using the first and second trends, to automatically determine a HF risk of the patient using a weighted combination of the first and second gait features each weighted by the respective weight factors, and to provide an output of the automatically determined HF risk to a display for presentation to a user or to adjust or initiate a process of the system.

2. The system of claim 1, comprising:
a motion sensor coupled to the gait analyzer circuit and configured to sense the gait or balance information of the patient; and
at least one physiologic sensor configured to sense physiologic information different from the gait or balance information,
wherein the HF detector circuit is configured to automatically determine the HE risk of the patient further using the sensed physiologic information.

3. The system of claim 2, comprising an ambulatory device that includes the motion sensor, the gait analyzer circuit, and the HF detector circuit,
wherein the motion sensor includes at least one of:
an accelerometer;
a gyroscope;
a magnetometer;
an inclinometer;
a goniometer,
an electromagnetic tracking system;
a global positioning system sensor;
a force sensor;
a strain gauge sensor;
an electromyography sensor; or
a camera configured to record an image or video of patient motion.

4. The system of claim 2, comprising an ambulatory device that includes the gait analyzer circuit and the HF detector circuit, wherein the motion sensor is incorporated in a mobile device communicatively coupled to the ambulatory device.

5. The system of claim 1, wherein the first and second gait features each include at least one of:
velocity;
time to peak velocity;
stride length;
stride width;
swing time;
single limb support time;
double limb stance;
gait autonomy;
cadence;
foot-hip angle; or
trunk-pelvis rotation angle.

6. The system of claim 1, wherein at least one of the first or the second gait feature includes a gait pattern indicative of a degree of continuity or an inter-limb coordination during locomotion.

7. The system of claim 1, comprising a multi-axis accelerometer configured to sense body acceleration of the patient during locomotion, and wherein the gait analyzer circuit is configured to generate a multi-dimensional representation of the sensed body acceleration; and
the HF detector circuit is configured to automatically determine the HF risk using the generated multi-dimensional representation.

8. The system of claim 7, wherein the multi-dimensional representation includes a three-dimensional (3D) contour representing body accelerations in three directions, and the HF detector circuit is configured to automatically determine the HF risk using a geometric feature taken from the 3D contour.

9. The system of claim 1, wherein the gait analyzer circuit is configured to identify one or more gait phases within a gait cycle, and to generate the first or the second gait feature using the received gait or balance information during the identified one or more gait phases.

10. The system of claim 1, wherein:
the gait analyzer circuit is configured to generate a composite trend using the first trend of the first gait feature and the second trend of the second gait feature; and
the HF detector circuit is configured to automatically determine the HF risk of the patient using the generated composite trend.

11. The system of claim 1, comprising an implantable medical device (IMD) that includes one or more of the gait analyzer circuit or the HF detector circuit.

12. The system of claim 1, wherein the HF detector circuit is configured to trigger one or more physiologic sensors to sense physiologic information in response to at least one of the first or the second generated gait feature satisfies a condition, and to automatically determine the HF risk further using the sensed physiologic information.

13. The system of claim 1, comprising a therapy circuit configured to initiate or adjust a HF therapy in accordance with the determined HF risk.

14. A system for monitoring heart failure (HF) status of a patient, the system comprising:
a gait analyzer circuit configured to receive gait or balance information of a patient during locomotion, to generate a gait feature including a multi-dimensional representation of body acceleration during locomotion using the received gait or balance information; and
a HF detector circuit configured to automatically determine a HF risk of the patient using the generated multi-dimensional representation and to provide an output of the automatically determined HF risk to a display for presentation to a user or to adjust or initiate a process of the system.

15. The system of claim 14, comprising a multi-axis accelerometer configured to sense body acceleration during locomotion, and wherein the gait analyzer circuit is configured to generate the multi-dimensional representation of body acceleration during locomotion.

16. The system of claim 14, wherein the multi-dimensional representation includes a three-dimensional (3D) contour representing body accelerations in three directions, and the HF detector circuit is configured to automatically determine the HF risk using a geometric feature taken from the 3D contour.

17. The system of claim 16, wherein the geometric feature includes at least one of:
a location of a centroid of the 3D contour;
a diameter of 3D contour; or
an area or a volume of the 3D contour.

18. The system of claim 14, comprising a therapy circuit configured to initiate or adjust a HF therapy in accordance with the determined HF risk.

19. A system for monitoring heart failure (HF) status of a patient, the system comprising:
a gait analyzer circuit configured to receive gait or balance information of a patient during locomotion, to generate two or more gait features using the received gait or balance information, and to generate a composite gait trend over time using the two or more gait features; and
a HF detector circuit configured to automatically determine a HF risk of the patient using the generated composite gait trend and to provide an output of the automatically determined HF risk to a display for presentation to a user or to adjust or initiate a process of the system.

20. The system of claim 19, wherein the HF detector circuit is configured to
- trigger one or more physiologic sensors to sense physiologic information in response to at least one of the generated gait features satisfies a condition; and
- automatically determine the HF risk further using the sensed physiologic information.

* * * * *